(12) United States Patent
Kaasgaard et al.

(10) Patent No.: US 12,129,498 B2
(45) Date of Patent: *Oct. 29, 2024

(54) STABILIZED ENDOGLUCANASE VARIANTS

(71) Applicant: Novozymes A/S, Bagsvaerd (DK)

(72) Inventors: Svend Gunnar Kaasgaard, Svoklunde (DK); Frank Winther Rasmussen, Roskilde (DK); Roland Alexander Pache, Valby (DK); Lars Anderson, Malmo (SE); Mette Louise Dissing Overgaard, Copenhagen (DK); Thomas Agersten Poulsen, Ballerup (DK); Lars Giger, Valby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/302,506

(22) Filed: Apr. 18, 2023

(65) Prior Publication Data

US 2023/0287380 A1 Sep. 14, 2023

Related U.S. Application Data

(62) Division of application No. 17/041,631, filed as application No. PCT/EP2019/059460 on Apr. 12, 2019, now Pat. No. 11,661,592.

(30) Foreign Application Priority Data

Apr. 19, 2018 (EP) .................................... 18168189
Jan. 23, 2019 (EP) .................................... 19153173

(51) Int. Cl.
*C12N 9/42* (2006.01)
*C11D 3/386* (2006.01)
*C12N 9/50* (2006.01)
*C12N 15/80* (2006.01)

(52) U.S. Cl.
CPC ........ *C12N 9/2437* (2013.01); *C11D 3/38618* (2013.01); *C11D 3/38645* (2013.01); *C12N 9/50* (2013.01); *C12N 15/80* (2013.01); *C12Y 302/01004* (2013.01)

(58) Field of Classification Search
None
See application file for complete search history.

(56) References Cited

U.S. PATENT DOCUMENTS

| 6,001,639 | A | 12/1999 | Schulein | |
|---|---|---|---|---|
| 11,661,592 | B2 * | 5/2023 | Kaasgaard | ............... C12N 9/50 510/393 |
| 2010/0143967 | A1 | 6/2010 | Mcfarland | |
| 2013/0260420 | A1 | 10/2013 | Morant et al. | |
| 2014/0150137 | A1 | 5/2014 | Spodsberg et al. | |
| 2015/0353871 | A1 | 12/2015 | Oebro et al. | |
| 2017/0081615 | A1 | 3/2017 | Andersen | |
| 2017/0298302 | A1 | 10/2017 | Krogsgaard et al. | |
| 2017/0335243 | A1 | 11/2017 | Hansen et al. | |
| 2018/0171271 | A1 | 6/2018 | Skagerlind et al. | |
| 2018/0171544 | A1 | 6/2018 | Lai et al. | |
| 2019/0106690 | A1 | 4/2019 | Lai et al. | |
| 2021/0047628 | A1 | 2/2021 | Kaasgaard et al. | |

FOREIGN PATENT DOCUMENTS

| CA | 3007148 A1 | 8/2017 |
|---|---|---|
| CN | 101855345 A | 10/2010 |
| CN | 103534348 A | 1/2014 |
| CN | 103649308 A | 3/2014 |
| CN | 104789543 | 7/2015 |
| CN | 106133135 A | 11/2016 |
| CN | 106795507 A | 5/2017 |
| CN | 107849548 A | 3/2018 |
| CN | 107922896 A | 4/2018 |
| EP | 1350843 A2 | 10/2003 |
| WO | 1996029397 A1 | 9/1996 |
| WO | 2017084560 A1 | 5/2017 |
| WO | 2017097861 A1 | 6/2017 |
| WO | 2017106676 A1 | 6/2017 |
| WO | 2019201783 A1 | 10/2019 |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Accession AZX33567. Aug. 16, 2012 (Year: 2012).*
Ge et al., Guangdong Agricultural Science, 2013, 150-154, 9—Incl. En. Abstract.
Bornscheuer, 2011, Curr Protoc Protein Sci., Chapter 26, Unit 26.7.
Chica et al., Current Opinion in Biotechnology, 2005, 378-384, 16(4).
KOGA 2008 Appl Environ Microbiol 74(13) 4210-4217, 4210-4217, 74(13).
Singh et al., Current Protein and Peptide Science, 2017, 1-11, 18.
Takashima, 1999, Accession No. 093782.
Vandeputte, 2014. EBI No. A0A084FZY4.
Whisstock et al., Quarterly Reviews of Biophysics, 2003, 307-340, 36(3).
Witkowski et al., Biochemistry, 1999, 11643-11650, 38(36).
Yoshikuni 2007 Curr Opin Chem Biol 11(2) 233-239, 233-239, 11(2).

\* cited by examiner

*Primary Examiner* — Christian L Fronda
(74) *Attorney, Agent, or Firm* — Kelly K. Reynolds

(57) ABSTRACT

Disclosed are variants of a cellulase having improved stability in the presence of a protease, and the use of such variants in laundry.

15 Claims, No Drawings
Specification includes a Sequence Listing.

STABILIZED ENDOGLUCANASE VARIANTS

CROSS-REFERENCE TO RELATED APPLICATIONS

This application is a continuation application of U.S. application Ser. No. 17/041,631, filed Sep. 25, 2020 and published as US Patent Application Publication 2021/0047628 on Feb. 18, 2021, which is a 35 U.S.C. 371 national application of international application no. PCT/EP2019/059460 filed Apr. 12, 2019 and published as International Publication WO2019/201783 on Oct. 24, 2019, which application claims priority or the benefit under 35 U.S.C. 119 of application no. EP 18168189.1 and EP 19153173.0 filed Apr. 19, 2018 and Jan. 23, 2019, the contents of which are fully incorporated herein by reference.

REFERENCE TO SEQUENCE LISTING

This application contains a Sequence Listing in computer readable form. The contents of the electronic sequence listing created on Apr. 18, 2023, named SQ_ST26.xml and 6 KB in size, is hereby incorporated by reference in its entirety.

FIELD OF THE INVENTION

The present invention relates to variants of a cellulase having improved stability, in particular stability in the presence of detergent and/or protease. Further, the invention relates to liquid detergent compositions comprising a stabilized cellulase variant.

BACKGROUND OF THE INVENTION

Cellulases have in several years been used in detergents due to the observed benefits in the laundry process, such as color clarification, prevent redeposition, anti-pilling/pill removal and improved whiteness.

In some applications a complex cellulase enzyme composition is used, where the composition comprises more than one cellulose degrading enzymes, selected among endoglucanases, cellobiohydrolases and beta-glucosidases are used, whereas other applications uses enzyme compositions mainly comprising one or more endoglucanases are used.

WO 1996/029397 discloses family 45 endoglucanases for detergent use.

Most commercial detergent compositions comprise proteases that improved the removal of many common strains. However, proteases also degrade other proteins available in the washing solution, including other enzymes such as cellulases.

It is therefore desirable to provide cellulases such as cellulase variants having increased stability in the presence of proteases.

SUMMARY OF THE INVENTION

The invention provides variants having endoglucanase activity and having at least 80% sequence identity to SEQ ID NO: 1, SEQ ID NO: 2, SEQ ID NO: 3, or SEQ ID NO: 4, and where the stability in the presence of protease is increased in comparison with the endoglucanase having SEQ ID NO: 1, SEQ ID NO: 2, SEQ ID NO: 3, or SEQ ID NO: 4.

The invention further relates to polynucleotides and expression constructs comprising the polynucleotide; host cells comprising the polynucleotides or expression constructs and the use of such host cells for producing the variants of the invention.

Compositions, in particular detergent compositions comprising the variants, and the use of such compositions for laundering textiles are also disclosed.

Definitions

Dish washing composition: The term "dish washing composition" refers to compostions intended for cleaning dishes, table ware, pots, pans, cutlery and all forms of compositions for cleaning hard surfaces areas in kitchens. The present invention is not restricted to any particular type of dish wash composition or any particular detergent.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

Whiteness: The term "Whiteness" is defined herein as a broad term with different meanings in different regions and for different consumers. Loss of whiteness can e.g. be due to greying, yellowing, or removal of optical brighteners/hueing agents. Greying and yellowing can be due to soil redeposition, body soils, coloring from e.g. iron and copper ions or dye transfer. Whiteness might include one or several issues from the list below: colorant or dye effects; incomplete stain removal (e.g. body soils, sebum etc.); redeposition (greying, yellowing or other discolorations of the object) (removed soils re-associate with other parts of textile, soiled or unsoiled); chemical changes in textile during application; and clarification or brightening of colors.

"Color clarification: During washing and wearing loose or broken fibers can accumulate on the surface of the fabrics. One consequence can be that the colors of the fabric appear less bright or less intense because of the surface contaminations. Removal of the loose or broken fibers from the textile will partly restore the original colors and looks of the textile. By the term "color clarification", as used herein, is meant the partial restoration of the initial colors of textile."

"Anti-pilling: The term "anti-pilling" denotes removal of pills from the textile surface and/or prevention of formation of pills on the textile surface."

Cellulase: The term "cellulase" means an enzyme having cellulytic activity that catalyzes the hydrolysis of 1,4-beta-D-glucosidic linkages in cellulose. For purposes of the present invention, cellulytic activity is determined according to the procedure described in Materials and methods section. In one aspect, the variants of the present invention have at least 20%, e.g., at least 40%, at least 50%, at least 60%, at least 70%, at least 80%, at least 90%, at least 95%, or at least 100% of the cellulytic activity of the parent (or reference) peptide, for example, the mature polypeptide of SEQ ID NO: 1, SEQ ID NO: 2, SEQ ID NO: 3, or SEQ ID NO: 4.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has cellulytic activity. In one aspect, a fragment contains at least 260 amino acid residues (e.g., amino acids 1 to 260 of SEQ ID NO: 1, SEQ ID NO: 2, SEQ ID NO: 3, or SEQ ID NO: 4), at least 240 amino acid residues (e.g., amino acids 1 to 240 of SEQ ID NO: 1, SEQ ID NO: 2, SEQ ID NO: 3, or SEQ ID NO: 4), or at least the residues corresponding to the catalytic domain, e.g. 210, 211, 212, or 216 amino acid residues (e.g., amino acids 1 to 212 of SEQ ID NO: 1 or amino acids 1 to 216 of SEQ ID NO: 1, amino acids 1 to 211 of SEQ ID NO: 2 or amino acids 1 to 212 of SEQ ID NO: 2, amino acids 1 to 211 of SEQ ID NO: 3 or amino acids 1 to 210 of SEQ ID NO: 3, amino acids 1 to 211 of SEQ ID NO: 4).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to stability in the presence of protease.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent cellulase: The term "parent" or "parent cellulase" means any polypeptide with cellulytic activity to which an alteration is made to produce the enzyme variants of the present invention.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment–Total Number of Gaps in Alignment)

Variant: The term "variant" means a polypeptide having cellulytic activity comprising a substitution at one or more (e.g., several) positions. A substitution means replacement of the amino acid occupying a position with a different amino acid. The variants of the present invention have at least 20%, e.g., at least 40%, at least 50%, at least 60%, at least 70%, at least 80%, at least 90%, at least 95%, or at least 100% of the cellulytic activity of the parent (or reference) peptide, for example, the mature polypeptide of SEQ ID NO: 1, SEQ ID NO: 2, or SEQ ID NO: 3, or SEQ ID NO: 4.

Conventions for Designation of Variants

For purposes of the present invention, the mature polypeptide disclosed in SEQ ID NO: 1 is used to determine the corresponding amino acid residue in another cellulase. The amino acid sequence of another cellulase is aligned with the mature polypeptide disclosed in SEQ ID NO: 1, and based on the alignment, the amino acid position number corresponding to any amino acid residue in the mature polypeptide disclosed in SEQ ID NO: 1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another cellulase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Bioloqy 537: 39-64; Katoh and Toh, 2010, Bioinformatics 26: 1899-1900), and EMBOSS EMMA employing ClustalW (1.83 or later; Thompson et al., 1994, Nucleic Acids Research 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G—K—A    |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to cellulase variants, comprising a substitution at one or more (e.g., several) positions corresponding to positions: 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219 of the polypeptide having the sequence of SEQ ID NO: 1, wherein the variant has cellulytic activity.

Variants

The present invention also provides cellulase variants, comprising a substitution at one or more (e.g., several) positions corresponding to positions: 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219 of SEQ ID NO: 1, wherein the variant has cellulytic activity.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent cellulase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 1, SEQ ID NO: 2, SEQ ID NO: 3, or SEQ ID NO: 4.

In one aspect, the number of substitutions in the variants of the present invention is 1-20, e.g., 1-10 and 1-5, such as 1, 2, 3, 4, 5, 6, 7, 8, 9 or 10 substitutions.

In another aspect, a variant comprises a substitution at one or more (e.g., several) positions corresponding to positions: 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219. In another aspect, a variant comprises an alteration at two positions corresponding to any of positions 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219. In another aspect, a variant comprises an alteration at three positions corresponding to any of positions: 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219. In another aspect, a variant comprises an alteration at four, five, six, seven, eight, nine, ten or even more positions each corresponding to one of the positions: 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219.

In another aspect, the variant comprises or consists of a substitution at a position corresponding to one of positions: 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219 in SEQ ID NO: 1. In another aspect, the amino acid at this position is substituted with Ala, Arg, Asn, Asp, Cys, Gln, Glu, Gly, His, Ile, Leu, Lys, Met, Phe, Pro, Ser, Thr, Trp, Tyr, or Val.

Following substitutions are preferred:
the amino acid in position 4 is substituted with Ala (X4A);
the amino acid in position 6 is substituted with Met, Asn, Trp, or Tyr (X6M, X6N, X6W, or X6Y);
the amino acid in position 25 is substituted with Gly (X25G);
the amino acid in position 32 is substituted with Ser (X32S);

the amino acid in position 37 is substituted with Trp (X37W);

the amino acid in position 41 is substituted with Thr (X41T);

the amino acid in position 44 is substituted with Asp (X44D);

the amino acid in position 51 is substituted with Asn (X51N);

the amino acid in position 56 is substituted with Ala (X56A);

the amino acid in position 77 is substituted with Asn (X77N);

the amino acid in position 80 is substituted with Lys or Leu (X80K or X80L);

the amino acid in position 82 is substituted with Ile (X82I);

the amino acid in position 83 is substituted with Asp (X83D);

the amino acid in position 85 is substituted with Asp, Ile, Lys, Met or Val (X85D, X85I, X85K, X85M or X85V);

the amino acid in position 91 is substituted with Phe (X91F);

the amino acid in position 93 is substituted with Met (X93M);

the amino acid in position 94 is substituted with Lys, Leu, Asn or Gln (X94K, X94L, X94N or X94Q);

the amino acid in position 96 is substituted with Ala, Phe, Arg or Val (X96A, X96F, X96R or X96V);

the amino acid in position 98 is substituted with Thr (X98T);

the amino acid in position 100 is substituted with Ala, Ser or Thr (X100A, X100S or X100T);

the amino acid in position 101 is substituted with Asp, Glu, His, Lys, Leu, Arg or Val (X101D, X101E, X101H, X101K, X101L, X101R or X101V);

the amino acid in position 103 is substituted with Ala, Leu, Met or Gln (X103A, X103L, X103M or X103Q);

the amino acid in position 104 is substituted with Ala, Asp, Ile, Lys, Leu, Met, Lys, Asn, Gln, Arg, Val or Tyr (X104A, X104D, X104I, X104K, X104L, X104M, X104K, X104N, X104Q, X104R, X104V or X104Y);

the amino acid in position 114 is substituted with Ala, Phe, His, Ile, Lys, Leu, Met, Arg, Trp or Tyr (X114A, X114F, X114H, X114I, X114K, X114L, X114M, X114R, X114W or X114Y);

the amino acid in position 117 is substituted with Arg (X117R);

the amino acid in position 118 is substituted with Ile (X118I);

the amino acid in position 132 is substituted with Lys, Leu, Arg, or Val (X132K, X132L, X132R, or X132V);

the amino acid in position 133 is substituted with Tyr (X133Y);

the amino acid in position 134 is substituted with Asp (X134D);

the amino acid in position 137 is substituted with Ala, Asp, Glu, Gly, Lys, Met, Asn or Arg (X137A, X137D, X137E, X137G, X137K, X137M, X137N or X137R);

the amino acid in position 146 is substituted with Asp, Glu, Gly, Lys, Arg, Ser or Thr (X146D, X146E, X146G, X146K, X146R, X146S or X146T);

the amino acid in position 147 is substituted with Asp, Glu, Lys, Arg or Tyr (X147D, X147E, X147K, X147R or X147Y);

the amino acid in position 148 is substituted with Phe or Trp (X148F or X148W);

the amino acid in position 152 is substituted with Asp, Lys or Arg (X152D, X152K or X152R);

the amino acid in position 156 is substituted with Glu (X156E);

the amino acid in position 159 is substituted with Asp or Glu (X159D or X159E);

the amino acid in position 162 is substituted with Glu (X162E);

the amino acid in position 166 is substituted with Ser (X166S);

the amino acid in position 169 is substituted with Phe, Trp or Tyr (X169F, X169W or X169Y);

the amino acid in position 179 is substituted with Ser or Thr (X179S or X179T);

the amino acid in position 183 is substituted with Val (X183V);

the amino acid in position 184 is substituted with Ala, Leu or Met (X184A, X184L or X184M); the amino acid in position 186 is substituted with Arg (X186R);

the amino acid in position 194 is substituted with Ser or Leu (X194S or X194L);

the amino acid in position 201 is substituted with Arg (X201R);

the amino acid in position 202 is substituted with Gly or Leu (X202G or X202L);

the amino acid in position 211 is substituted with His, Lys, Leu, Asn, Pro, Val or Trp (X211H, X211K, X211L, X211N, X211P, X211V or X211W);

the amino acid in position 213 is substituted with Gln (X213Q); or the amino acid in position 219 is substituted with Trp (X219W).

In a particular preferred embodiment, the parent cellulase is the polypeptide having the sequence of SEQ ID NO: 1, and the variant comprising one or more substitutions selected among:

the amino acid in position 4, Ser, is substituted with Ala (S4A);

the amino acid in position 6, Gln, is substituted with Met, Asn, Trp, or Tyr (Q6M, Q6N, Q6W, or Q6Y);

the amino acid in position 25, Ala, is substituted with Gly (A25G);

the amino acid in position 32, Ala, is substituted with Ser (A32S);

the amino acid in position 37, Phe, is substituted with Trp (F37W);

the amino acid in position 41, Ser, is substituted with Thr (S41T);

the amino acid in position 44, Asn, is substituted with Asp (N44D);

the amino acid in position 51, Gly, is substituted with Asn (G51N);

the amino acid in position 56, Ser, is substituted with Ala (S56A);

the amino acid in position 77, Ser, is substituted with Asn (S77N);

the amino acid in position 80, Gly, is substituted with Lys or Leu (G80K or G80L);

the amino acid in position 82, Ser, is substituted with Ile (S82I);

the amino acid in position 83, Glu, is substituted with Asp (G83D);

the amino acid in position 85, Ser, is substituted with Asp, Ile, Lys, Met or Val (S85D, S85I, S85K, S85M or S85V);

the amino acid in position 91, Tyr, is substituted with Phe (Y91F);

the amino acid in position 93, Leu, is substituted with Met (L93M);

the amino acid in position 94, Thr, is substituted with Lys, Leu, Asn or Gln (T94K, T94L, T94N or T94Q);

the amino acid in position 96, Thr, is substituted with Ala, Phe, Arg or Val (T96A, T96F, T96R or T96V);

the amino acid in position 98, Gly, is substituted with Thr (G98T);

the amino acid in position 100, Val, is substituted with Ala, Ser or Thr (V100A, V100S or V100T);

the amino acid in position 101, Ala, is substituted with Asp, Glu, His, Lys, Leu, Arg or Val (A101D, A101E, A101H, A101K, A101L, A101R or A101V);

the amino acid in position 103, Lys, is substituted with Ala, Leu, Met or Gln (K103A, K103L, K103M or K103Q);

the amino acid in position 104, Thr, is substituted with Ala, Asp, Ile, Lys, Leu, Met, Lys, Asn, Gln, Arg, Val or Tyr (T104A, T104D, T104I, T104K, T104L, T104M, T104K, T104N, T104Q, T104R, T104V or T104Y);

the amino acid in position 114, Gly, is substituted with Ala, Phe, His, Ile, Lys, Leu, Met, Arg, Trp or Tyr (G114A, G114F, G114H, G114I, G114K, G114L, G114M, G114R, G114W or G114Y);

the amino acid in position 117, Gly, is substituted with Arg (G117R);

the amino acid in position 118, Ser, is substituted with Ile (S118I);

the amino acid in position 132, Ile, is substituted with Lys, Leu, Arg, or Val (I132K, I132L, I132R, or I132V);

the amino acid in position 133, Phe, is substituted with Tyr (F133Y);

the amino acid in position 134, Asn, is substituted with Asp (N134D);

the amino acid in position 137, Ser, is substituted with Ala, Asp, Glu, Gly, Lys, Met, Asn or Arg (S137A, S137D, S137E, S137G, S137K, S137M, S137N or S137R);

the amino acid in position 146, Ala, is substituted with Asp, Glu, Gly, Lys, Arg, Ser or Thr (A146D, A146E, A146G, A146K, A146R, A146S or A146T);

the amino acid in position 147, Gln, is substituted with Asp, Glu, Lys, Arg or Tyr (Q147D, Q147E, Q147K, Q147R or Q147Y);

the amino acid in position 148, Tyr, is substituted with Phe or Trp (Y148W or Y148F);

the amino acid in position 152, Ser, is substituted with Asp, Lys or Arg (S152D, S152K or S152R);

the amino acid in position 156, Gln, is substituted with Glu (Q156E);

the amino acid in position 159, Ser, is substituted with Asp or Glu (S159D or S159E);

the amino acid in position 162, Ala, is substituted with Glu (A162E);

the amino acid in position 166, Pro, is substituted with Ser (P166S);

the amino acid in position 169, Gln, is substituted with Phe, Trp or Tyr (Q169F, Q169W or Q169Y);

the amino acid in position 179, Asp, is substituted with Ser or Thr (D179S or D179T);

the amino acid in position 183, Phe, is substituted with Val (F183V);

the amino acid in position 184, Thr, is substituted with Ala, Leu or Met (T184A, T184L or T184M);

the amino acid in position 186, Gln, is substituted with Arg (Q186R);

the amino acid in position 194, Ile, is substituted with Ser or Leu (I194S or I194L);

the amino acid in position 201, Lys, is substituted with Arg (K201R);

the amino acid in position 202, Arg, is substituted with Gly or Leu (R202G or R202L);

the amino acid in position 211, Phe, is substituted with His, Lys, Leu, Asn, Pro, Val or Trp (F211H, F211K, F211L, F211N, F211P, F211V or F211 W);

the amino acid in position 213, Pro, is substituted with Gln (P213Q); or the amino acid in position 219, Gly, is substituted with Trp (G219W).

In some embodiments, the variants comprises 2 or more, e.g. 3, 4, 5, 6, 7, 8, 9 or 10 substitutions in position corresponding to positions 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219 of the polypeptide having the sequence of SEQ ID NO: 1, SEQ ID NO: 2, SEQ ID NO: 3 or SEQ ID NO: 4, wherein the variant has cellulytic activity.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulytic activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. The catalytic residues of the cellulase having the amino acid sequence of SEQ ID NO: 1 have been identified as Asp 12 and Asp 122. The variants may consist of 216 to 278 amino acids, e.g., 216 to 240 amino acids.

In an embodiment, the variant has improved stability in the presence of a protease compared to the parent enzyme. Preferably the variant has improved stability in the presence of a protease and a surfactant, such as a detergent composition; in comparison with the parent cellulase.

Stability in the Presence of Protease

The variants of the invention have improved stability in the presence of protease in comparison with the parent cellulase.

Stability in the presence of protease is beneficial for cellulases used under conditions where protease is presence because it extend the time where the cellulases are functional and active and can exert the function it was intended to do.

One preferred use of the variants of the invention is in detergents, where proteases typically are included to improve the detergency. The improved stability of the variants of the invention means that the variants can exert the cellulytic activity for a longer time during the laundry process compared with the parent cellulase, and thereby provide an improved detergency benefit compared with the parent cellulase.

For liquid detergent compositions, the variants of the invention further have the benefit that improved stability in the presence of protease means that the liquid detergent composition comprising a protease and further comprising a variant of the invention have a longer shelf life in comparison with the same liquid detergent composition comprising the parent cellulase.

Stability in presence of protease may be determined by incubating a given cellulase under defined conditions in the presence of a protease, measuring the cellulytic activity in after the incubation and comparing it with a sample of the cellulase that has not been incubated with protease.

Another method for determining the stability in presence of protease is to prepare two identical test tubes comprising the given cellulase to be tested in a defined solution comprising a protease, incubating one test tube under elevated temperature e.g. in the range of 30-60° C. (stress) whereas the other tube is incubated at low temperature e.g. in the range of 0-5° C. (non-stress). After the incubation both samples are analysed for cellulytic activity and the residual activity is determined as Residual activity (%)=(Activity,stress/Activity,non-stress)*100.

According to the invention it is preferred to determine the residual activity in 50% liquid detergent A containing 0.166 v/v-% protease, where the samples are incubated for 16 hours at 40° C. (stress) and 5° C. (non-stress) before the activity is determined. Residual activity is determined as:

Residual activity (%)=(Activity,sample incubated at 40° C./Activity,sample incubated at 5° C.)*100

This method is illustrated in more details in Example 1.

The variants of the invention have higher residual activities than the parent cellulases. In one embodiment has the variants of the invention at least 10% higher Residual activity compared with the parent cellulase, e.g. at least 20% higher Residual activity, e.g. at least 30% higher Residual activity, e.g. at least 40% higher Residual activity, e.g. at least 50% higher Residual activity, e.g. at least 60% higher Residual activity, e.g. at least 70% higher Residual activity, e.g. at least 80% higher Residual activity, e.g. at least 90% higher Residual activity or at least 100% higher Residual activity, compared with the parent.

It may be convenient to calculate the Residual Activity Ratio (RAR) when the stability of a variant is compared with a reference cellulase, typically the parent cellulase:

Residual Activity Ratio (RAR)=(RA,variant)/(RA, reference)

For the variants of the invention the RAR, using the parent cellulase as reference, is higher than 1, i.e. the RAR is higher than 1+ the standard deviation for the assay, preferably higher than 1+two times the standard deviation for the assay.

Expressed in another way, the variants of the invention have a RAR, using the parent cellulase as reference, of at least 1.1, preferably at least 1.2, preferably at least 1.3, preferably at least 1.4, preferably at least 1.5, preferably at least 1.6, preferably at least 1.7, preferably at least 1.8, preferably at least 1.9, preferably at least 2 or even higher.

Parent Cellulases

The parent cellulase may be a polypeptide having cellulytic activity and having at least 80%, at least 85%, at least 90%, at least 91%, at least 92%, at least 93%, at least 94%, at least 95%, at least 96%, at least 97%, at least 98%, at least 99%, or 100%, sequence identity to the polypeptide having the sequence of SEQ ID NO: 1, SEQ ID NO: 2, SEQ ID NO: 3, or SEQ ID NO: 4. In one aspect, the amino acid sequence of the parent differs by up to 10 amino acids, e.g., 1, 2, 3, 4, 5, 6, 7, 8, 9, or 10, from the mature polypeptide of SEQ ID NO: 1.

In another aspect, the parent comprises or consists of the amino acid sequence of SEQ ID NO: 1, SEQ ID NO: 2, SEQ ID NO: 3, or SEQ ID NO: 4.

In another aspect, the parent comprises or consists of amino acids 1 to 212 of SEQ ID NO: 1 or amino acids 1 to 216 of SEQ ID NO: 1, amino acids 1 to 211 of SEQ ID NO: 2 or amino acids 1 to 212 of SEQ ID NO: 2, or amino acids 1 to 210 of SEQ ID NO: 3 or amino acids 1 to 211 of SEQ ID NO: 3, or amino acids 1 to 211 of SEQ ID NO: 4.

In another aspect, the parent is a fragment of the mature polypeptide of SEQ ID NO: 2 containing at least 200 amino acid residues, e.g., at least 216 and at least 240 amino acid residues.

In another embodiment, the parent is an allelic variant of the mature polypeptide of SEQ ID NO: 1, SEQ ID NO: 2, SEQ ID NO: 3, or SEQ ID NO: 4.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly. The parent may be a bacterial cellulase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* cellulase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* cellulase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* cellulase.

In another aspect, the parent is a *Streptococcus equisimilis, Streptococcus pyogenes, Streptococcus uberis*, or *Streptococcus equi* subsp. *Zooepidemicus* cellulase.

In another aspect, the parent is a *Streptomyces achromogenes, Streptomyces avermitilis, Streptomyces coelicolor, Streptomyces griseus*, or *Streptomyces lividans* cellulase.

The parent may be a fungal cellulase. For example, the parent may be a yeast cellulase such as a *Candida, Kluyveromyces, Pichia, Saccharomyces, Schizosaccharomyces*, or *Yarrowia* cellulase; or a filamentous fungal cellulase such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptosphaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* cellulase.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cellulase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* cellulase.

In another aspect, the parent is a *Thielavia terrestris* cellulase, e.g., the cellulase of SEQ ID NO: 1 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having cellulytic activity, comprising: (a) introducing into a parent cellulase a substitution at one or more (e.g., several) positions corresponding to positions: 4, 6, 25, 32, 37, 41, 44, 51, 56, 77, 80, 82, 83, 85, 91, 93, 94, 96, 98, 100, 101, 103, 104, 114, 117, 118, 132, 133, 134, 137, 146, 147, 148, 152, 156, 159, 162, 166, 169, 179, 183, 184, 186, 194, 201, 202, 211, 213 or 219 of the mature polypeptide of SEQ ID NO: 1, wherein the variant has cellulytic activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7:127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/ or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylllA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase Ill, *Trichoderma reesei* endoglucanase IV, Trichoderma reesei endoglucanase V, Trichoderma reesei xylanase I, Trichoderma reesei xylanase II, Trichoderma reesei beta-xylosidase, as well as the NA2-tpi promoter (a modified promoter from an Aspergillus neutral alpha-amylase gene in which the untranslated leader has been replaced by an untranslated leader from an Aspergillus triose phosphate isomerase gene; non-limiting examples include modified promoters from an Aspergillus niger neutral alpha-amylase gene in which the untranslated leader has been replaced by an untranslated leader from an Aspergillus nidulans or Aspergillus oryzae triose phosphate isomerase gene); and mutant, truncated, and hybrid promoters thereof.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for Bacillus clausii alkaline protease (aprH), Bacillus licheniformis alpha-amylase (amyL), and Escherichia coli ribosomal RNA (rrnB).

Preferred terminators for filamentous fungal host cells are obtained from the genes for Aspergillus nidulans anthranilate synthase, Aspergillus niger glucoamylase, Aspergillus niger alpha-glucosidase, Aspergillus oryzae TAKA amylase, and Fusarium oxysporum trypsin-like protease.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a Bacillus thuringiensis crylllA gene (WO 94/25612) and a Bacillus subtilis SP82 gene (Hue et al., 1995, Journal of Bacteriology 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for Aspergillus nidulans anthranilate synthase, Aspergillus niger glucoamylase, Aspergillus niger alpha-glucosidase, Aspergillus oryzae TAKA amylase, and Fusarium oxysporum trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for Bacillus NCIB 11837 maltogenic amylase, Bacillus licheniformis subtilisin, Bacillus licheniformis beta-lactamase, Bacillus stearothermophilus alpha-amylase, Bacillus stearothermophilus neutral proteases (nprT, nprS, nprM), and Bacillus subtilis prsA. Further signal peptides are described by Simonen and Palva, 1993, Microbiological Reviews 57: 109-137.

Effective signal peptide coding sequences for filamentous fungal host cells are the signal peptide coding sequences obtained from the genes for Aspergillus niger neutral amylase, Aspergillus niger glucoamylase, Aspergillus oryzae TAKA amylase, Humicola insolens cellulase, Humicola insolens endoglucanase V, Humicola lanuginosa lipase, and Rhizomucor miehei aspartic proteinase.

Useful signal peptides for yeast host cells are obtained from the genes for Saccharomyces cerevisiae alpha-factor and Saccharomyces cerevisiae invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for Bacillus subtilis alkaline protease (aprE), Bacillus subtilis neutral protease (nprT), Myceliophthora thermophila laccase (WO 95/33836), Rhizomucor miehei aspartic proteinase, and Saccharomyces cerevisiae alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium*

*bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

Detergent Compositions

In one embodiment, the invention is directed to detergent compositions comprising an enzyme of the present invention in combination with one or more additional cleaning composition components. The choice of additional components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment, the invention is directed to an ADW (Automatic Dish Wash) compositions comprising an enzyme of the present invention in combination with one or more additional ADW composition components. The choice of additional components is within the skill of the artisan and includes conventional ingredients, including the exemplary non-limiting components set forth below.

Enzyme of the Present Invention

In one embodiment of the present invention, the polypeptide of the present invention may be added to a detergent composition in an amount corresponding to 0.001-200 mg of protein, such as 0.005-100 mg of protein, preferably 0.01-50 mg of protein, more preferably 0.05-20 mg of protein, even more preferably 0.1-10 mg of protein per liter of wash liquor.

The enzyme(s) of the detergent composition of the invention may be stabilized using conventional stabilizing agents, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708.

A polypeptide of the present invention may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 5% to 60% by weight, such as about 5% to about 50%, or about 10% to about 50%, or about 20% to about 50%. The surfactant(s) is chosen based on the desired cleaning application, and may include any conventional surfactant(s) known in the art.

When included therein the detergent will usually contain from about 5% to about 60% by weight of one or more anionic surfactants, such as from about 5% to about 40%, including from about 10% to about 25%, Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ether-sulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salts of fatty acids (soap) or fatty acids, and combinations thereof.

When included therein the detergent will usually contain from about from about 0.1% to about 10% by weigh of a cationic surfactant, for example from about 0.1% to about 5%, Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyl-dimethylammonium, alkyl quaternary ammonium compounds, alkoxylated quaternary ammonium (AQA) compounds, ester quats, and combinations thereof.

When included therein the detergent will usually contain from about 0.2% to about 60% by weight of a nonionic surfactant, for example from about 1% to about 40%, in particular from about 5% to about 20%, from about 3% to about 15%, Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), methylester ethoxylates (MEE), as well as products available under the trade names SPAN and TWEEN, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyldimethylbetaines, sulfobetaines, and combinations thereof.

Solvent system: For dissolution of the surfactant and other detergent ingredients, a solvent system is needed. Solvents are typically water, alcohols, polyols, sugars and/or mixtures thereof. Preferred solvents are water, glycerol, sorbitol, propylene glycol (MPG, 1,2-propanediol or 1,3-propane diol), dipropylene glycol (DPG), polyethylene glycol family (PEG300-600), hexylene glycol, inositol, mannitol, Ethanol, isopropanol, n-butoxy propoxy propanol, ethanolamines (monoethanol amine, diethanol amines and triethanol amines), sucrose, dextrose, glucose, ribose, xylose, and related mono and di pyranosides and furanosides.

The solvent system is present in typically totally 5-90%, 5-60%, 5-40%, 10-30% by weight.

The water content for unit doses wrapped in PVA film is typically in the range 1-15%, 2-12%, 3-10%, 5-10%.

The polyol content for unit doses wrapped in PVA film is typically in the range 5-50%, 10-40% or 20-30%.

In an embodiment, the surfactant is a non-naturally occurring surfactant.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants), however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming micellar, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65%, 0-20%; or 0.5-5% of a detergent builder or co-builder, or a mixture thereof. In a dish wash detergent, the level of builder is typically 10-65%, particularly 20-40%. The builder and/or co-builder may particularly be a chelating agent that forms water-soluble complexes with Ca and Mg. Any builder and/or co-builder known in the art for use in laundry detergents may be utilized. Nonlimiting examples are citrate, sodium carbonate, sodium bicarbonate and sodium citrate, Examples of phosphonates include 1-Hydroxy Ethylidene-1,1-Diphosphonic Acid (HEDP, etidronic acid), Diethylenetriamine Penta(Methylene Phosphonic acid) (DTPMP), Ethylene diamine tetra(methylene phosphonic acid) (EDTMPA), amino tris(methylenephosphonic acid) (ATMP), Nitrilo trimethylene phosphonic acid (NTMP), 2-Amino ethyl phosphonic acid (AEPn), Dimethyl methylphosphonate (DMPP), Tetramethylene diamine tetra(methylene phosphonic acid) (TDTMP), Hexamethylene diamine tetra(methylene phosphonic acid) (HDTMP), Phosphonobutane-tricarboxylic acid (PBTC), N-(phosphonomethyl) iminodiacetic acid (PMIDA), 2-carboxyethyl phosphonic acid (CEPA), 2-Hydroxy phosphonocarboxylic acid (HPAA) and Amino-tris-(methylene-phosphonic acid) (AMP). L-glutamic acid N,N-diacetic acid tetra sodium salt (GLDA)., methylglycinediacetic acid (MGDA). Non-limiting examples of builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl) iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phe-nylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N', N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

In an embodiment, the builder or co-builder is a non-naturally occurring builder or co-builder.

Bleaching Systems

The detergent may contain 0-30% by weight, such as about 1% to about 20%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that it is environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

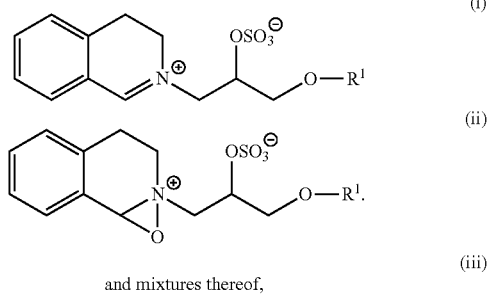

and mixtures thereof, wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) preformed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

In an embodiment, the bleaching system is a non-naturally occurring bleaching system.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

In an embodiment, the polymer is a non-naturally occurring polymer

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Color Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more [additional] enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from Bacillus or Humicola, particularly B. agaradhaerens, B. licheniformis, B. halodurans, B. clausii, or H. insolens. Suitable mannanases are described in WO 1999/064619. A commercially available mannanase is Mannaway (Novozymes A/S).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Eng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from Bacillus such as Bacillus lentus, B. alkalophilus, B. subtilis, B. amyloliquefaciens, Bacillus pumilus and Bacillus gibsonii described in; U.S. Pat. No. 7,262,042 and WO09/021867, and subtilisin Novo, subtilisin Carlsberg, Bacillus licheniformis, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the Fusarium protease described in WO89/06270, WO94/25583 and WO05/040372, and the chymotrypsin proteases derived from Cellumonas described in WO05/052161 and WO05/052146.

A further preferred protease is the alkaline protease from Bacillus lentus DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from Bacillus amyloliquefaciens.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (Bacillus alkalophilus subtilisin) from Kao.

Lipases and Cutinases:

Suitable lipases and cutinases include those of bacterial or fungal origin. Chemically modified or protein engineered mutant enzymes are included. Examples include lipase from Thermomyces, e.g. from T. lanuginosus (previously named Humicola lanuginosa) as described in EP258068 and EP305216, cutinase from Humicola, e.g. H. insolens (WO96/13580), lipase from strains of Pseudomonas (some of these now renamed to Burkholderia), e.g. P. alcaligenes or P. pseudoalcaligenes (EP218272), P. cepacia (EP331376), P. sp. strain SD705 (WO95/06720 & WO96/27002), P. wisconsinensis (WO96/12012), GDSL-type Streptomyces lipases (WO10/065455), cutinase from Magnaporthe grisea (WO10/107560), cutinase from Pseudomonas mendocina (U.S. Pat. No. 5,389,536), lipase from Thermobifida fusca (WO11/084412), Geobacillus stearothermophilus lipase (WO11/084417), lipase from Bacillus subtilis (WO11/084599), and lipase from Streptomyces griseus (WO 11/150157) and S. pristinaespiralis (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to Candida antarctica lipase A (WO10/111143), acyltransferase from Mycobacterium smegmatis (WO05/56782), perhydrolases from the CE 7 family (WO09/67279), and variants of the M. smegmatis perhydrolase in particular the S54V variant used in the commercial product Gentle Power Bleach from Huntsman Textile Effects Pte Ltd (WO10/100028).

Amylases:

Suitable amylases which can be used together with the variants of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T491+G107A+H156Y+A181T+N190F+I201F+ A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T131I+T165I+K178L+T182G+Y305R+ G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Plus™, Natalase™ and BAN™ (from Novozymes A/S), and Rapidase™, Purastar™/Effectenz™, Powerase™, Preferenz S1000™ Preferenz S110™ and Preferenz S100™ (from Genencor International Inc./DuPont).

Peroxidases/Oxidases:

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

- Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.
- Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.
- Fluorescent whitening agent—The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers—are structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, and solvents.

Protease Inhibitor

The protease inhibitor maybe any compound which stabilises or inhibits the protease so that the protease or other enzyme(s) in the laundry soap bar are not degraded. Examples of protease inhibitors are aprotinin, bestatin, calpain inhibitor I and II, chymostatin, leupeptin, pepstatin, phenylmethanesulfonyl fluoride (PMSF), boric acid, borate, borax, boronic acids, phenylboronic acids such as 4-formylphenylboronic acid (4-FPBA), peptide aldehydes or hydrosulfite adducts or hemiacetal adducts thereof and peptide trifluromethyl ketones. There may be one or more protease inhibitors, such as 5, 4, 3, 2 or 1 inhibitor(s) of which at least one is a peptide aldehyde, a hydrosulfite adduct or a hemiacetal adduct thereof.

Peptide Aldehyde Inhibitor

The peptide aldehyde may have the formula $P\text{-}(A)_y\text{-}L\text{-}(B)_x\text{-}B^0\text{-}H$ or a hydrosulfite adduct or hemiacetal adduct thereof, wherein:
i. H is hydrogen;
ii. $B^0$ is a single amino acid residue with L- or D-configuration of the formula $-NH-CH(R)-C(=O)-$;
iii. x is 1, 2 or 3 for $(B)_x$, and B is independently a single amino acid connected to $B^0$ via the C-terminal of the B amino acid
iv. L is absent or L is independently a linker group of the formula $-C(=O)-$, $-C(=O)-C(=O)-$, $-C(=S)-$, $-C(=S)-C(=S)-$ or $-C(=S)-C(=O)-$;
v. y is 0, 1 or 2 for $(A)_y$, and A is independently a single amino acid residue connected to L via the N-terminal of the A amino acid, with the proviso that if L is absent then A is absent;
vi. P is selected from the group consisting of hydrogen and an N-terminal protection group, with the proviso that if L is absent then P is an N-terminal protection group; vii. R is independently selected from the group consisting of $C_{1-6}$ alkyl, $C_{6-10}$ aryl or $C_{7-10}$ arylalkyl optionally substituted with one or more, identical or different, substituent's R';

viii. R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$; and ix. R" is a C$_{1-6}$ alkyl group.

x may be 1, 2 or 3 and therefore B may be 1, 2 or 3 amino acid residues respectively. Thus, B may represent B$^1$, B$^2$-B$^1$ or B$^3$-B$^2$-B$^1$, where B$^3$, B$^2$ and B$^1$ each represent one amino acid residue. y may be 0, 1 or 2 and therefore A may be absent, or 1 or 2 amino acid residues respectively having the formula A$^1$ or A$^2$-A$^1$ wherein A$^2$ and A$^1$ each represent one amino acid residue.

B$^0$ may be a single amino acid residue with L- or D-configuration, which is connected to H via the C-terminal of the amino acid, wherein R is a C$_{1-6}$ alkyl, C$_{6-10}$ aryl or C$_{7-10}$ arylalkyl side chain, such as methyl, ethyl, propyl, isopropyl, butyl, isobutyl, phenyl or benzyl, and wherein R may be optionally substituted with one or more, identical or different, substituent's R'. Particular examples are the D- or L-form of arginine (Arg), 3,4-dihydroxyphenylalanine, isoleucine (Ile), leucine (Leu), methionine (Met), norleucine (Nle), norvaline (Nva), phenylalanine (Phe), m-tyrosine, p-tyrosine (Tyr) and valine (Val). A particular embodiment is when B$^0$ is leucine, methionine, phenylalanine, p-tyrosine and valine.

B$^1$, which is connected to B$^0$ via the C-terminal of the B$^1$ amino acid, may be an aliphatic, hydrophobic and/or neutral amino acid. Examples of B$^1$ are alanine (Ala), cysteine (Cys), glycine (Gly), isoleucine (Ile), leucine (Leu), norleucine (Nle), norvaline (Nva), proline (Pro), serine (Ser), threonine (Thr) and valine (Val). Particular examples of B$^1$ are alanine, glycine, isoleucine, leucine and valine. A particular embodiment is when B$^1$ is alanine, glycine or valine.

If present, B$^2$, which is connected to B$^1$ via the C-terminal of the B$^2$ amino acid, may be an aliphatic, hydrophobic, neutral and/or polar amino acid. Examples of B$^2$ are alanine (Ala), arginine (Arg), capreomycidine (Cpd), cysteine (Cys), glycine (Gly), isoleucine (Ile), leucine (Leu), norleucine (Nle), norvaline (Nva), phenylalanine (Phe), proline (Pro), serine (Ser), threonine (Thr), and valine (Val). Particular examples of B$^2$ are alanine, arginine, capreomycidine, glycine, isoleucine, leucine, phenylalanine and valine. A particular embodiment is when B$^2$ is arginine, glycine, leucine, phenylalanine or valine.

B$^3$, which if present is connected to B$^2$ via the C-terminal of the B$^3$ amino acid, may be a large, aliphatic, aromatic, hydrophobic and/or neutral amino acid. Examples of B$^3$ are isoleucine (Ile), leucine (Leu), norleucine (Nle), norvaline (Nva), phenylalanine (Phe), phenylglycine, tyrosine (Tyr), tryptophan (Trp) and valine (Val). Particular examples of B$^3$ are leucine, phenylalanine, tyrosine and tryptophan.

The linker group L may be absent or selected from the group consisting of —C(=O)—, —C(=O)—C(=O)—, —C(=S)—, —C(=S)—C(=S)— or —C(=S)—C(=O)—. Particular embodiments are when L is absent or L is a carbonyl group —C(=O)—.

A$^1$, which if present is connected to L via the N-terminal of the amino acid, may be an aliphatic, aromatic, hydrophobic, neutral and/or polar amino acid. Examples of A$^1$ are alanine (Ala), arginine (Arg), capreomycidine (Cpd), glycine (Gly), isoleucine (Ile), leucine (Leu), norleucine (Nle), norvaline (Nva), phenylalanine (Phe), threonine (Thr), tyrosine (Tyr), tryptophan (Trp) and valine (Val). Particular examples of A$^1$ are alanine, arginine, glycine, leucine, phenylalanine, tyrosine, tryptophan and valine. A particular embodiment is when B$^2$ is leucine, phenylalanine, tyrosine or tryptophan.

The A$^2$ residue, which if present is connected to A$^1$ via the N-terminal of the amino acid, may be a large, aliphatic, aromatic, hydrophobic and/or neutral amino acid. Examples of A$^2$ are arginine (Arg), isoleucine (Ile), leucine (Leu), norleucine (Nle), norvaline (Nva), phenylalanine (Phe), phenylglycine, Tyrosine (Tyr), tryptophan (Trp) and valine (Val). Particular examples of A$^2$ are phenylalanine and tyrosine.

The N-terminal protection group P (if present) may be selected from formyl, acetyl (Ac), benzoyl (Bz), trifluoroacetyl, methoxysuccinyl, aromatic and aliphatic urethane protecting groups such as fluorenylmethyloxycarbonyl (Fmoc), methoxycarbonyl, (fluoromethoxy)carbonyl, benzyloxycarbonyl (Cbz), t-butyloxycarbonyl (Boc) and adamantyloxycarbonyl; p-methoxybenzyl carbonyl (Moz), benzyl (Bn), p-methoxybenzyl (PMB), p-methoxyphenyl (PMP), methoxyacetyl, methylamino carbonyl, methylsulfonyl, ethylsulfonyl, benzylsulfonyl, methylphosphoramidyl (MeOP(OH)(=O)) and benzylphosphoramidyl (PhCH$_2$OP(OH)(=O)).

The general formula of the peptide aldehyde may also be written: P-A$^2$-A$^1$-L-B$^3$-B$^2$B$^1$-B$^0$—H, where P, A$^2$, A$^1$, L, B$^3$, B$^2$, B$^1$ and B$^0$ are as defined above.

In the case of a tripeptide aldehyde with a protection group (i.e. x=2, L is absent and A is absent), P is preferably acetyl, methoxycarbonyl, benzyloxycarbonyl, methylamino carbonyl, methylsulfonyl, benzylsulfonyl and benzylphosphoramidyl. In the case of a tetrapeptide aldehyde with a protection group (i.e. x=3, L is absent and A is absent), P is preferably acetyl, methoxycarbonyl, methylsulfonyl, ethylsulfonyl and methylphosphoramidyl.

Suitable peptide aldehydes are described in WO94/04651, WO95/25791, WO98/13458, WO98/13459, WO98/13460, WO98/13461, WO98/13462, WO07/141736, WO07/145963, WO09/118375, WO10/055052 and WO11/036153.

More particularly, the peptide aldehyde may be

Cbz-Arg-Ala-Tyr-H (L-Alaninamide, N2-[(phenylmethoxy)carbonyl]-L-arginyl-N-[(1S)-1-formyl-2-(4-hydroxyphenyl)ethyl]-), Ac-Gly-Ala-Tyr-H (L-Alaninamide, N-acetylglycyl-N-[(1S)-1-formyl-2-(4-hydroxyphenyl)ethyl]-)

Cbz-Gly-Ala-Tyr-H (L-Alaninamide, N-[(phenylmethoxy)carbonyl]glycyl-N-[(1S)-1-formyl-2-(4-hydroxyphenyl)ethyl]-), Cbz-Gly-Ala-Leu-H (L-Alaninamide, N-[(phenylmethoxy)carbonyl]glycyl-N-[(1S)-1-formyl-3-methylbutyl]-), Cbz-Val-Ala-Leu-H (L-Alaninamide, N-[(phenylmethoxy)carbonyl]-L-valyl-N-[(1S)-1-formyl-3-methylbutyl]-), Cbz-Gly-Ala-Phe-H (L-Alaninamide, N-[(phenylmethoxy)carbonyl]glycyl-N-[(1S)-1-formyl-2-phenylethyl]-), Cbz-Gly-Ala-Val-H (L-Alaninamide, N-[(phenylmethoxy)carbonyl]glycyl-N-[(1S)-1-formyl-2-methylpropyl]-), Cbz-Gly-Gly-Tyr-H (Glycinamide, N-[(phenylmethoxy)carbonyl]glycyl-N-[(1S)-1-formyl-2-(4-hydroxyphenyl)ethyl]-), Cbz-Gly-Gly-Phe-H (Glycinamide, N-[(phenylmethoxy)carbonyl]glycyl-N-[(1S)-1-formyl-2-phenylethyl]-), Cbz-Arg-Val-Tyr-H (L-Valinamide, N2-[(phenylmethoxy)carbonyl]-L-arginyl-N-[(1S)-1-formyl-2-(4-hydroxyphenyl)ethyl]-), Cbz-Leu-Val-Tyr-H (L-Valinamide, N-[(phenylmethoxy)carbonyl]-L-leucyl-N-[(1S)-1-formyl-2-(4-hydroxyphenyl)ethyl]-)

Ac-Leu-Gly-Ala-Tyr-H (L-Alaninamide, N-acetyl-L-leucylglycyl-N-[(1S)-1-formyl-2-(4-hydroxyphenyl)ethyl]-), Ac-Phe-Gly-Ala-Tyr-H (L-Alaninamide, N-acetyl-L-phenylalanylglycyl-N-[(1S)-1-formyl-2-(4-hydroxyphenyl)-), Ac-Tyr-Gly-Ala-Tyr-H (L-Alaninamide, N-acetyl-L-tyrosylglycyl-N-[(1S)-1-formyl-2-(4-hydroxyphenyl)ethyl]-), Ac-Phe-Gly-Ala-Leu-H (L-Alaninamide, N-acetyl-L-phenylalanylglycyl-N-[(1S)-1-formyl-3-methylbutyl]-), Ac-Phe-Gly-Ala-Phe-H (L-Alaninamide, N-acetyl-L-phenylalanylglycyl-N-[(1S)-1-formyl-2-phenylethyl]-)

Ac-Phe-Gly-Val-Tyr-H (L-Valinamide, N-acetyl-L-phenylalanylglycyl-N-[(1S)-1-formyl-2-(4-hydroxyphenyl)ethyl]-), Ac-Phe-Gly-Ala-Met-H (L-Alaninamide, N-acetyl-L-phenylalanylglycyl-N-[(1S)-1-formyl-3-(methylthio)propyl]-), Ac-Trp-Leu-Val-Tyr-H (L-Valinamide, N-acetyl-L-tryptophyl-L-leucyl-N-[(1S)-1-formyl-2-(4-hydroxyphenyl)ethyl]-), MeO—CO-Val-Ala-Leu-H (L-Alaninamide, N-(methoxycarbonyl)-L-valyl-N-[(1S)-1-formyl-3-methylbutyl]-)

MeNHCO-Val-Ala-Leu-H (L-Alaninamide, N-(aminomethylcarbonyl)-L-valyl-N-[(1S)-1-formyl-3-methylbutyl]-), MeO—CO-Phe-Gly-Ala-Leu-H (L-Alaninamide, N-(methoxycarbonyl)-L-phenylalanylglycyl-N-[(1S)-1-formyl-3-methylbutyl]-), MeO—CO-Phe-Gly-Ala-Phe-H (L-Alaninamide, N-(methoxycarbonyl)-L-phenylalanylglycyl-N-[(1S)-1-formyl-2-phenylethyl]-), MeSO2-Phe-Gly-Ala-Leu-H (L-Alaninamide, N-(methylsulfonyl)-L-phenylalanylglycyl-N-[(1S)-1-formyl-3-methylbutyl]-), MeSO2-Val-Ala-Leu-H (L-Alaninamide, N-(methylsulfonyl)-L-valyl-N-[(1S)-1-formyl-3-methylbutyl]-), PhCH2O—P(OH)(O)-Val-Ala-Leu-H (L-Alaninamide, N-[hydroxy(phenylmethoxy)phosphinyl]-L-valyl-N-[(1S)-1-formyl-3-methylbutyl]-), EtSO2-Phe-Gly-Ala-Leu-H (L-Alaninamide, N-(ethylsulfonyl)-L-phenylalanylglycyl-N-[(1S)-1-formyl-3-methylbutyl]-), PhCH2SO2-Val-Ala-Leu-H (L-Alaninamide, N-[(phenylmethyl)sulfonyl]-L-valyl-N-[(1S)-1-formyl-3-methylbutyl]-), PhCH2O—P(OH)(O)-Leu-Ala-Leu-H (L-Alaninamide, N-[hydroxy(phenylmethoxy)phosphinyl]-L-leucyl-N-[(1S)-1-formyl-3-methylbutyl]-), PhCH2O—P(OH)(O)-Phe-Ala-Leu-H (L-Alaninamide, N-[hydroxy(phenylmethoxy)phosphinyl]-L-phenylalanyl-N-[(1S)-1-formyl-3-methylbutyl]-), or MeO—P(OH)(O)-Leu-Gly-Ala-Leu-H; (L-Alaninamide, N-(hydroxymethoxyphosphinyl)-L-leucylglycyl-N-[(1S)-1-formyl-3-methylbutyl]-).

A preferred example is Cbz-Gly-Ala-Tyr-H.

Further examples of such peptide aldehydes include

α-MAPI (3,5,8,11-Tetraazatridecanoic acid, 6-[3-[(aminoiminomethyl)amino]propyl]-12-formyl-9-(1-methylethyl)-4,7,10-trioxo-13-phenyl-2-(phenylmethyl)-, (2S,6S,9S,12S)—

L-Valinamide, N2-[[(1-carboxy-2-phenylethyl)amino]carbonyl]-L-arginyl-N-(1-formyl-2-phenylethyl)-, [1(S),2(S)]—; L-Valinamide, N2-[[[(1S)-1-carboxy-2-phenylethyl]amino]carbonyl]-L-arginyl-N-[(1S)-1-formyl-2-phenylethyl]-(9Cl); SP-Chymostatin B), β-MAPI (L-Valinamide, N2-[[[(1S)-1-carboxy-2-phenylethyl]amino]carbonyl]-L-arginyl-N-[(1R)-1-formyl-2-phenylethyl]-L-Valinamide, N2-[[(1-carboxy-2-phenylethyl)amino]carbonyl]-L-arginyl-N-(1-formyl-2-phenylethyl)-, [1(S),2(R)]—), Phe-C(=O)-Arg-Val-Tyr-H (L-Valinamide, N2-[[[(1S)-1-carboxy-2-phenylethyl]amino]carbonyl]-L-arginyl-N-[(1S)-1-formyl-2-(4-hydroxyphenyl)ethyl]-(9Cl)), Phe-C(=O)-Gly-Gly-Tyr-H, (3,5,8,11-Tetraazatridecanoic acid, 12-formyl-13-(4-hydroxyphenyl)-4,7,10-trioxo-2-(phenylmethyl)-, (2S,12S)—), Phe-C(=O)-Gly-Ala-Phe-H, (3,5,8,11-Tetraazatridecanoic acid, 12-formyl-9-methyl-4,7,10-trioxo-13-phenyl-2-(phenylmethyl)-, (2S,9S,12S)—), Phe-C(=O)-Gly-Ala-Tyr-H (3,5,8,11-Tetraazatridecanoic acid, 12-formyl-13-(4-hydroxyphenyl)-9-methyl-4,7,10-trioxo-2-(phenylmethyl)-, (2S,9S,12S)—), Phe-C(=O)-Gly-Ala-Leu-H, (3,5,8,11-Tetraazapentadecanoic acid, 12-formyl-9,14-dimethyl-4,7,10-trioxo-2-(phenylmethyl)-, (2S,9S,12S)—), Phe-C(=O)-Gly-Ala-Nva-H, (3,5,8,11-Tetraazapentadecanoic acid, 12-formyl-9-methyl-4,7,10-trioxo-2-(phenylmethyl)-, (2S,9S,12S)—), Phe-C(=O)-Gly-Ala-Nle-H (3,5,8,11-Tetraazahexadecanoic acid, 12-formyl-9-methyl-4,7,10-trioxo-2-(phenylmethyl)-, (2S,9S,12S)—), Tyr-C(=O)-Arg-Val-Tyr-H (L-Valinamide, N2-[[[(1S)-1-carboxy-2-(4-hydroxyphenyl)ethyl]amino]carbonyl]-L-arginyl-N-[(1S)-1-formyl-2-(4-hydroxyphenyl)ethyl]-(9Cl))

Tyr-C(=O)-Gly-Ala-Tyr-H (3,5,8,11-Tetraazatridecanoic acid, 12-formyl-13-(4-hydroxyphenyl)-2-[(4-hydroxyphenyl)methyl]-9-methyl-4,7,10-trioxo-, (2S,9S,12S)—)

Phe-C(=S)-Arg-Val-Phe-H, (3,5,8,11-Tetraazatridecanoic acid, 6-[3-[(aminoiminomethyl)amino]propyl]-12-formyl-9-(1-methylethyl)-7,10-dioxo-13-phenyl-2-(phenylmethyl)-4-thioxo-, (2S,6S,9S,12S)—), Phe-C(=S)-Arg-Val-Tyr-H, (3,5,8,11-Tetraazatridecanoic acid, 6-[3-[(aminoiminomethyl)amino]propyl]-12-formyl-13-(4-hydroxyphenyl)-9-(1-methylethyl)-7,10-dioxo-2-(phenylmethyl)-4-thioxo-, (2S,6S,9S,12S)—), Phe-C(=S)-Gly-Ala-Tyr-H, (3,5,8,11-Tetraazatridecanoic acid, 12-formyl-13-(4-hydroxyphenyl)-9-methyl-7,10-dioxo-2-(phenylmethyl)-4-thioxo-, (2S,9S,12S)—), Antipain (L-Valinamide, N2-[[(1-carboxy-2-phenylethyl)amino]carbonyl]-L-arginyl-N-[4-[(aminoiminomethyl)amino]-1-formylbutyl]-), GE20372A (L-Valinamide, N2-[[[(1S)-1-carboxy-2-(4-hydroxyphenyl)ethyl]amino]carbonyl]-L-arginyl-N-[(1S)-1-formyl-2-phenylethyl]-

L-Valinamide, N2-[[[1-carboxy-2-(4-hydroxyphenyl)ethyl]amino]carbonyl]-L-arginyl-N-(1-formyl-2-phenylethyl)-, [1(S),2(S)]—), GE20372B (L-Valinamide, N2-[[[(1S)-1-carboxy-2-(4-hydroxyphenyl)ethyl]amino]carbonyl]-L-arginyl-N-[(1R)-1-formyl-2-phenylethyl]-

L-Valinamide, N2-[[[1-carboxy-2-(4-hydroxyphenyl)ethyl]amino]carbonyl]-L-arginyl-N-(1-formyl-2-phenylethyl)-, [1(S),2(R)]—), Chymostatin A (L-Leucinamide, (2S)-2-[(4S)-2-amino-3,4,5,6-tetrahydro-4-pyrimidinyl]-N-[[[(1S)-1-carboxy-2-phenylethyl]amino]carbonyl]glycyl-N-(1-formyl-2-phenylethyl)-

L-Leucinamide, (2S)-2-[(4S)-2-amino-1,4,5,6-tetrahydro-4-pyrimidinyl]-N-[[[(1S)-1-carboxy-2-phenylethyl]amino]carbonyl]glycyl-N-(1-formyl-2-phenylethyl)-(9Cl); L-Leucinamide, L-2-(2-amino-1,4,5,6-tetrahydro-4-pyrimidinyl)-N-[[(1-carboxy-2-phenylethyl)amino]carbonyl]glycyl-N-(1-formyl-2-phenylethyl)-, stereoisomer), Chymostatin B (L-Valinamide, (2S)-2-[(4S)-2-amino-3,4,5,6-tetrahydro-4-pyrimidinyl]-N-[[[(1S)-1-carboxy-2-phenylethyl]amino]carbonyl]glycyl-N-(1-formyl-2-phenylethyl)-

L-Valinamide, (2S)-2-[(4S)-2-amino-1,4,5,6-tetrahydro-4-pyrimidinyl]-N-[[[(1S)-1-carboxy-2-phenylethyl]amino]carbonyl]glycyl-N-(1-formyl-2-phenylethyl)-(9Cl); L-Valinamide, L-2-(2-amino-1,4,5,6-tetrahydro-4-pyrimidinyl)-N-[[(1-carboxy-2-phenylethyl)amino]carbonyl]glycyl-N-(1-formyl-2-phenylethyl)-, stereoisomer), and Chymostatin C (L-Isoleucinamide, (2S)-2-[(4S)-2-amino-3,4,5,6-tetrahydro-4-pyrimidinyl]-N-[[[(1S)-1-carboxy-2-phenylethyl]amino]carbonyl]glycyl-N-(1-formyl-2-phenylethyl)-

L-Isoleucinamide, (2S)-2-[(4S)-2-amino-1,4,5,6-tetrahydro-4-pyrimidinyl]-N-[[[(1S)-1-carboxy-2-phenylethyl]amino]carbonyl]glycyl-N-(1-formyl-2-phenylethyl)-(9Cl); L-Isoleucinamide, L-2-(2-amino-1,4,5,6-tetrahydro-4-pyrimidinyl)-N-[[(1-carboxy-2-phenylethyl)amino]carbonyl]glycyl-N-(1-formyl-2-phenylethyl)-, stereoisomer).

Peptide Aldehyde Adducts

Instead of a peptide aldehyde, the protease inhibitor may be an adduct of a peptide aldehyde. The adduct maybe a hydrosulfite adduct having the formula P-(A)$_y$-L-(B)$_x$N(H)—CHR—CH(OH)—SO$_3$M, wherein P, A, y, L, B, x and R are defined as above, and M is H or an alkali metal, preferably Na or K. Alternatively, the adduct may be a hemiacetal having the formula P-(A)$_y$-L-(B)$_x$—N(H)—CHR—CH(OH)—OR, wherein P, A, y, L, B, x and R are defined as above. A preferred embodiment is a hydrosulfite adduct wherein P=Cbz, B$^2$=Gly; B$^1$=Ala; B$^0$=Tyr (so R=PhCH$_2$, R'=OH), x=2, y=0, L=A=absent and M=Na (Cbz-Gly-Ala-N(H)—CH(CH$_2$-p-C$_6$H$_4$OH)—CH(OH)—SO$_3$Na, L-Alaninamide, N-[(phenylmethoxy)carbonyl]glycyl-N-[2-hydroxy-1-[(4-hydroxyphenyl)methyl]-2-sulfoethyl]-, sodium salt (1:1)).

The general formula of the hydrosulfite adduct of a peptide aldehyde may also be written: P-A$^2$-A$^1$-L-B$^3$-B$^2$-B$^1$—N(H)—CHR—CH(OH)—SO$_3$M, where P, A$^2$, A$^1$, L, B$^3$, B$^2$, B$^1$, R and M are as defined above.

Alternatively, the adduct of a peptide aldehyde can be Cbz-Gly-Ala-N(H)—CH(CH$_2$-p-C$_6$H$_4$OH)—CH(OH)—SO$_3$Na (Sodium (2S)—[(N—{N-[(benzyloxy)carbonyl]glycyl}-L-alaninyl)amino]-1-hydroxy-3-(4-hydroxyphenyl) propane-1-sulfonate) or Cbz-Gly-Ala-N(H)—CH(CH$_2$Ph)-CH(OH)—SO$_3$Na (Sodium (2S)—[(N—{N-[(benzyloxy)carbonyl]glycyl}-L-alaninyl)amino]-1-hydroxy-3-(phenyl) propane-1-sulfonate) or "MeO-CO_Val-Ala-N(H)—CH(CH2CH(CH$_3$)$_2$)—CH(OH)—SO$_3$Na (Sodium (2S)—[(N—{N-[(benzyloxy)carbonyl]glycyl}-L-alaninyl)amino]-1-hydroxy-3-(2-propanyl)propane-1-sulfonate).

Other preferred peptide aldehyde bisulfites are

Cbz-Arg-Ala-NHCH(CH$_2$C$_6$H$_4$OH)C(OH)(SO$_3$M)-H where M=Na,

Ac-Gly-Ala-NHCH(CH$_2$C$_6$H$_4$OH)C(OH)(SO$_3$M)-H, where M=Na,

Cbz-Gly-Ala-NHCH(CH$_2$C$_6$H$_4$OH)C(OH)(SO$_3$M)-H, where M=Na (L-Alaninamide, N-[(phenylmethoxy)carbonyl]glycyl-N-[2-hydroxy-1-[(4-hydroxyphenyl)methyl]-2-sulfoethyl]-, sodium salt (1:1)), Cbz-Gly-Ala-NHCH(CH$_2$CH(CH$_3$)$_2$))C(OH)(SO$_3$M)-H, where M=Na, Cbz-Val-Ala-NHCH(CH$_2$CH(CH$_3$)$_2$))C(OH)(SO$_3$M)-H, where M=Na, Cbz-Gly-Ala-NHCH(CH$_2$Ph)C(OH)(SO$_3$M)-H, where M=Na, Cbz-Gly-Ala-NHCH(CH(CH$_3$)$_2$)C(OH)(SO$_3$M)-H, where M=Na, Cbz-Gly-Gly-NHCH(CH$_2$C$_6$H$_4$OH)C(OH)(SO$_3$M)-H, where M=Na, Cbz-Gly-Gly-NHCH(CH$_2$Ph)C(OH)(SO$_3$M)-H, where M=Na, Cbz-Arg-Val-NHCH(CH$_2$C$_6$H$_4$OH)C(OH)(SO$_3$M)-H, where M=Na, Cbz-Leu-Val-NHCH(CH$_2$C$_6$H$_4$OH)C(OH)(SO$_3$M)-H, where M=Na, Ac-Leu-Gly-Ala-NHCH(CH$_2$C$_6$H$_4$OH)C(OH)(SO$_3$M)-H, where M=Na, Ac-Phe-Gly-Ala-NHCH(CH$_2$C$_6$H$_4$OH)C(OH)(SO$_3$M)-H, where M=Na, Ac-Tyr-Gly-Ala-NHCH(CH$_2$C$_6$H$_4$OH)C(OH)(SO$_3$M)-H, where M=Na, Ac-Phe-Gly-Ala-NHCH(CH$_2$CH(CH$_3$)$_2$))C(OH)(SO$_3$M)-H, where M=Na, Ac-Phe-Gly-Ala-NHCH(CH$_2$Ph)C(OH)(SO$_3$M)-H, where M=Na, Ac-Phe-Gly-Val-NHCH(CH$_2$C$_6$H$_4$OH)C(OH)(SO$_3$M)-H, where M=Na, Ac-Phe-Gly-Ala-NHCH(CH$_2$CH$_2$SCH$_3$)(SO$_3$M)-H, where M=Na, Ac-Trp-Leu-Val-NHCH(CH$_2$C$_6$H$_4$OH)C(OH)(SO$_3$M)-H, where M=Na, MeO—CO-Val-Ala-NHCH(CH$_2$CH(CH$_3$)$_2$))C(OH)(SO$_3$M)-H, where M=Na, MeNCO-Val-Ala-NHCH(CH$_2$CH(CH$_3$)$_2$))C(OH)(SO$_3$M)-H, where M=Na, MeO—CO-Phe-Gly-Ala-NHCH(CH$_2$CH(CH$_3$)$_2$))C(OH)(SO$_3$M)-H, where M=Na, MeO—CO-Phe-Gly-Ala-NHCH(CH$_2$Ph)C(OH)(SO$_3$M)-H, where M=Na, MeSO$_2$-Phe-Gly-Ala-NHCH(CH$_2$CH(CH$_3$)$_2$))C(OH)(SO$_3$M)-H, where M=Na, MeSO$_2$—Val-Ala-NHCH(CH$_2$CH(CH$_3$)$_2$))C(OH)(SO$_3$M)-H, where M=Na, PhCH$_2$O(OH)(O)P-Val-Ala-NHCH(CH$_2$CH(CH$_3$)$_2$))C(OH)(SO$_3$M)-H, where M=Na, EtSO$_2$-Phe-Gly-Ala-NHCH(CH$_2$CH(CH$_3$)$_2$))C(OH)(SO$_3$M)-H, where M=Na, PhCH$_2$SO$_2$—Val-Ala-NHCH(CH$_2$CH(CH$_3$)$_2$))C(OH)(SO$_3$M)-H, where M=Na, PhCH$_2$O(OH)(O)P-Leu-Ala-NHCH(CH$_2$CH(CH$_3$)$_2$))C(OH)(SO$_3$M)-H, where M=Na, PhCH$_2$O(OH)(O)P-Phe-Ala-NHCH(CH$_2$CH(CH$_3$)$_2$))C(OH)(SO$_3$M)-H, where M=Na, MeO(OH)(O)P-Leu-Gly-Ala-NHCH(CH$_2$CH(CH$_3$)$_2$))C(OH)(SO$_3$M)-H, where M=Na, and Phe-urea-Arg-Val-NHCH(CH$_2$C$_6$H$_4$OH)C(OH)(SO$_3$M)-H where M=Na.

Salt

The salt used in the bar is a salt of a monovalent cation and an organic anion. The monovalent cation may be for example $Na^+$, $K^+$ or $NH_4^+$. The organic anion may be for example formate, acetate, citrate or lactate. Thus a salt of a monovalent cation and an organic anion may be, for example, sodium formate, potassium formate, ammonium formate, sodium acetate, potassium acetate, ammonium acetate, sodium lactate, potassium lactate, ammonium lactate, mono-sodium citrate, di-sodium citrate, tri-sodium citrate, sodium potassium citrate, potassium citrate, ammonium citrate or the like. A particular embodiment is sodium formate.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Method of Producing the Composition

The present invention also relates to methods of producing the composition.

Uses

The present invention is also directed to methods for using the compositions thereof.

Use in Detergents.

The polypeptides of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

EXAMPLES

Materials and Methods

General methods of PCR, cloning, ligation nucleotides etc. are well-known to a person skilled in the art and may for example be found in in "Molecular cloning: A laboratory manual", Sambrook et al. (1989), Cold Spring Harbor lab, Cold Spring Harbor, NY; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

Composition of Model Detergent A (Liquid)

Composition of detergent A (liquid): Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w).

Protease

The protease used for the examples was Progress Uno® 101L, (Batch QHN00001) a commercially available protease product, available from Novozymes A/S, Bagsvaerd, and comprising an protease activity of 100 PRMU-U/g, or Progress Excel® 101L, (batch QIP00006) a commercially available protease product, available from Novozymes A/S, Bagsvaerd, and comprising an protease activity of 29 PRMU-E/g.

Assay for Cellulytic Activity

Cellulytic activity was determined using the Cellulase Assay Kit (CellG5 Method) provided from Megazyme, (Wicklow, Ireland; Product-code: K-CellG5-4V), following the manufacturer's instructions.

The CellG5 assay reagent for the measurement of endo-cellulase (endo-1,4-β-glucanase) contains two components;
1) 4,6-O-(3-Ketobutylidene)-4-nitrophenyl-β-D-cellopentaoside (BPNPG5) and 2) thermostable β-glucosidase. The ketone blocking group prevents any hydrolytic action by the β-glucosidase on BPNPG5.

Incubation with an endo-cellulase generates a non-blocked colorimetric oligosaccharide that is rapidly hydrolysed by the ancillary β-glucosidase. The rate of formation of 4-nitrophenol is therefore directly related to the hydrolysis of BPNPG5 by the endo-cellulase.

Example 1: Determining the Stability of Cellulase Variants

The stability of cellulase variants was measured in 50% liquid detergent A containing protease. The in-detergent stability was assessed by measuring the activity of the variants by the CellG5 kit after incubation of the enzyme-detergent mixture containing protease.
Temperature/Protease Stress Conditions in 50% Detergent A:

In a 96 well microplate (polystyrene), 60 μL of an enzyme solution (culture supernatant or purified enzyme diluted in buffer (100 mM Hepes; 0.01% Tween-20; pH 7.5)) was mixed with 60 μL of detergent A containing protease (0.166 v/v-% protease Progress Uno® 101L).

15 μL of the enzyme/detergent mix was transferred into two new 384 well microplates and sealed. One of the two identical plates were stored at 5° C. (reference) while the other was incubated at 40° C. (stress) for 16 hours. After incubation, 60 μL of assay buffer (100 mM Hepes; 0.01% Tween-20; pH 7.5) was added to the samples in both plates and mixed vigorously for the subsequent activity measurement.
Assaying Samples for Cellulolytic Activity (CellG5 Kit):

The enzymatic activity was measured by mixing 20 μL of the diluted enzyme-detergent mixture with 10 μL assay buffer (100 mM Hepes; 0.01% Tween-20; pH7.5) and 10 μL freshly prepared substrate solution in a UV-transparent 384 well microplate. Substrate solution of the CellG5 assay kit was prepared by mixing 10 μL of bottle #2 with 300 μL bottle #1.

The UV-absorbance (405 nm) was measured kinetically (every 2nd minute for 44 minutes) using a microplate reader (Tecan; Infinite, M1000, pro). The part of the curve displaying a constant absorbance increase was used to calculate the enzymatic activity of the sample (mOD/min). Thereafter the residual activity was calculated as the enzymatic activity of the sample incubated at 40° C. for 16 hours relative to the enzymatic activity in the corresponding sample stored at 5° C.

Residual activity (%)=(Activity,sample incubated at 40° C./Activity,sample incubated at 5° C.)*100

Residual Activity Ratio (RAR)

The residual activity ration for each condition was calculated by using the endoglucanase having SEQ ID NO: 1 as reference. The variants were tested as described above and the RAR calculated by using the following formula:

Residual Activity Ratio (RAR)=(RA,variant)/(RA, reference)

Example 2: Construction of Variants by Site-Directed Mutagenesis

Site-directed variants were constructed of the *Thielavia terrestris* cellulase (SEQ ID NO 1). The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence.

Mutagenic oligos were designed corresponding to the DNA sequence flanking the desired site(s) of mutation, separated by the DNA base pairs defining the insertions/deletions/substitutions, and purchased from an oligo vendor such as IDTDNA. In order to test the variants of the invention, the mutated DNA comprising a variant of the invention are integrated into a competent *A. oryzae* strain by homologous recombination, fermented using standard protocols (yeast extract based media, 4-5 days, 300C), and purified by chromatography.

Example 3: Residual Activity of Variants

The variants prepared in Example 2 were analysed for stability using the assay described in Example 1.

All variants having improved stability compared with the reference sequence was listed below. Table 1 lists variants having an improved stability compared with the reference, where a variant having a difference of the RAR to the mean of the standards of at least 2 times the standard deviation.

TABLE 1

Top hits with two standard deviations selection criteria
Residual activity ratio (RAR) is computed as percent residual activity relative to the mean percentresidual activity of the standards. The (StdZ) is computed as difference of the RAR to the mean of the standards divided by standard deviation of the RAR (standards). The hits were selected based on StdZ larger than 2 (StdZ > 2)

| Mutation | RAR |
|---|---|
| S4A | 1.11 |
| Q6N | 1.08 |
| Q6W | 1.08 |
| Q6M | 1.15 |
| F37W | 1.61 |
| G51N | 1.37 |
| G80K | 1.27 |
| G80L | 1.35 |
| S82I | 1.27 |
| E83D | 1.36 |
| S85K | 1.13 |
| S85D | 1.26 |
| S85M | 1.27 |
| S85V | 1.30 |
| S85I | 7.42 |
| T96A | 1.17 |
| T96V | 1.21 |
| T96R | 1.38 |
| T96F | 1.57 |
| G98T | 1.40 |
| V100T | 1.14 |
| V100A | 1.19 |
| V100S | 1.26 |
| A101K | 1.14 |
| A101L | 1.17 |
| A101D | 1.17 |
| A101R | 1.21 |
| A101V | 1.21 |
| K103Q | 1.28 |
| K103A | 3.06 |
| T104V | 1.29 |
| T104I | 1.32 |
| G114H | 1.28 |
| G114M | 1.47 |
| G114H | 1.48 |
| G114R | 1.59 |
| G114L | 1.70 |
| G114F | 2.16 |
| G114Y | 2.30 |
| G114W | 2.76 |
| I132L | 1.16 |
| I132L | 1.25 |
| I132K | 2.33 |
| F133Y | 1.32 |
| N134D | 2.69 |

TABLE 1-continued

Top hits with two standard deviations selection criteria
Residual activity ratio (RAR) is computed as percent residual
activity relative to the mean percent residual activity of the standards.
The (StdZ) is computed as difference of the RAR to the mean of
the standards divided by standard deviation of the RAR (standards).
The hits were selected based on StdZ larger than 2 (StdZ > 2)

| Mutation | RAR |
| --- | --- |
| S137M | 1.27 |
| S137A | 1.28 |
| S137N | 1.42 |
| S137E | 2.09 |
| S137R | 2.17 |
| S137D | 2.57 |
| S137K | 5.05 |
| A146T | 1.72 |
| A146G | 2.50 |
| A146R | 2.74 |
| A146S | 3.53 |
| A146K | 4.37 |
| A146E | 5.82 |
| A146D | 6.77 |
| A146H | 1.85 |
| A146N | 2.01 |
| Q147E | 1.59 |
| Q147T | 1.75 |
| Q147D | 4.32 |
| Q147K | 5.35 |
| Q147R | 6.32 |
| Y148W | 1.36 |
| S152R | 1.88 |
| S152K | 2.83 |
| S153D | 1.29 |
| S159D | 3.86 |
| S159E | 4.28 |
| A162E | 1.22 |
| P166S | 1.63 |
| Q169F | 1.27 |
| Q169W | 1.42 |
| Q169Y | 1.94 |
| D179S | 3.00 |
| D179T | 5.17 |
| I194S | 7.05 |
| R202L | 1.29 |
| P213Q | 1.54 |

Table 2 lists all variants having an improved stability, where an improved stability is determined as a RAR value larger than 1.1

TABLE 2

Hits selected based RAR larger than 1.1 (RAR ≥ 1.1)
Residual activity ratio (RAR) is computed as percent
residual activity relative to the mean percent residual
activity of the standards. Variants with a RAR-value
larger or equal to 1.1 were selected as hits.

| Mutation | RAR |
| --- | --- |
| S4A | 1.11 |
| Q6M | 1.15 |
| F37W | 1.61 |
| G51N | 1.37 |
| G80K | 1.27 |
| G80L | 1.35 |
| S82I | 1.27 |
| E83D | 1.36 |
| S85D | 1.26 |
| S85I | 7.42 |
| S85K | 1.13 |
| S85M | 1.27 |
| S85V | 1.30 |
| Y91F | 1.30 |
| L93M | 1.30 |
| T94K | 1.15 |
| T94L | 1.34 |
| T94N | 1.29 |
| T94Q | 1.16 |
| T96A | 1.17 |
| T96F | 1.57 |
| T96R | 1.38 |
| T96V | 1.21 |
| G98T | 1.40 |
| V100A | 1.19 |
| V100S | 1.26 |
| V100T | 1.14 |
| A101D | 1.17 |
| A101H | 1.12 |
| A101K | 1.14 |
| A101L | 1.17 |
| A101R | 1.21 |
| A101V | 1.21 |
| K103A | 3.06 |
| K103L | 1.22 |
| K103M | 1.12 |
| K103Q | 1.28 |
| T104A | 1.15 |
| T104D | 1.10 |
| T104I | 1.32 |
| T104K | 1.15 |
| T104L | 1.15 |
| T104M | 1.16 |
| T104N | 1.22 |
| T104Q | 1.20 |
| T104R | 1.20 |
| T104V | 1.29 |
| T104Y | 1.21 |
| G114A | 1.19 |
| G114F | 2.16 |
| G114H | 1.28 |
| G114H | 1.48 |
| G114I | 1.36 |
| G114L | 1.70 |
| G114M | 1.47 |
| G114R | 1.59 |
| G114W | 2.76 |
| G114Y | 2.30 |
| G117R | 1.11 |
| S118I | 1.11 |
| I132K | 2.33 |
| I132L | 1.16 |
| I132L | 1.25 |
| F133Y | 1.32 |
| N134D | 2.69 |
| S137A | 1.28 |
| S137D | 2.57 |
| S137E | 2.09 |
| S137G | 1.11 |
| S137K | 5.05 |
| S137M | 1.27 |
| S137N | 1.42 |
| S137R | 2.17 |
| A146D | 6.77 |
| A146E | 5.82 |
| A146G | 2.50 |
| A146K | 4.37 |
| A146R | 2.74 |
| A146S | 3.53 |
| A146T | 1.72 |
| A146N | 2.01 |
| Q147D | 4.32 |
| Q147E | 1.59 |
| Q147K | 5.35 |
| Q147R | 6.32 |
| Q147T | 1.75 |
| Y148W | 1.36 |
| S152D | 1.22 |
| S152K | 2.83 |

TABLE 2-continued

Hits selected based RAR larger than 1.1 (RAR ≥ 1.1)
Residual activity ratio (RAR) is computed as percent residual activity relative to the mean percent residual activity of the standards. Variants with a RAR-value larger or equal to 1.1 were selected as hits.

| Mutation | RAR |
| --- | --- |
| S152R | 1.88 |
| S153D | 1.29 |
| S159D | 3.86 |
| S159E | 4.28 |
| A162E | 1.22 |
| P166S | 1.63 |
| Q169F | 1.27 |
| Q169W | 1.42 |
| Q169Y | 1.94 |
| D179S | 3.00 |
| D179T | 5.17 |
| T184A | 1.11 |
| T184L | 1.11 |
| T184M | 1.11 |
| F185N | 1.15 |
| V188N | 1.18 |
| V188Q | 1.12 |
| I194S | 7.05 |
| R202G | 1.10 |
| R202L | 1.29 |
| F211H | 1.16 |
| F211K | 1.19 |
| F211L | 1.19 |
| F211N | 1.16 |
| F211P | 1.14 |
| F211V | 1.19 |
| F211W | 1.19 |
| P213Q | 1.54 |

Example 4: Construction of Variants by Site-Directed Mutagenesis

Site-directed variants were constructed of the *Humicola insolens* cellulase (SEQ ID NO: 2). The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence.

Mutagenic oligos were designed corresponding to the DNA sequence flanking the desired site(s) of mutation, separated by the DNA base pairs defining the insertions/deletions/substitutions, and purchased from an oligo vendor such as IDTDNA. In order to test the variants, the mutated DNA comprising a variant are integrated into a competent *A. oryzae* strain by homologous recombination, fermented using standard protocols (yeast extract based media, 4-5 days, 30° C.), and purified by chromatography.

Example 5: Residual Activity of Variants

The variants prepared in Example 4 were analysed for stability using the assay described in Example 1, except that a resulting dose of protease was: 0.45 v/v-% Progress Excel and the activity was calculated as the enzymatic activity of the sample incubated at 33.5° C. (instead of 40° C.) relative to the enzymatic activity in the corresponding sample stored at 5° C.

Table 3 lists residual activity, calculated as described in Example 1, of the parent (SEQ ID NO: 2) and the variants, as well as the correspondence of positions to the parent of SEQ ID NO: 2 and to SEQ ID NO: 1 used herein for numbering.

TABLE 3

| Mutation | Position of parent of SEQ ID NO: 2 | Correspondent position of SEQ ID NO: 1 (used for numbering) | Residual Activity (%) |
| --- | --- | --- | --- |
| SEQ ID NO: 2 | — | — | 11 |
| I131R | 131 | 132 | 47 |
| I131V | 131 | 132 | 25 |
| I131L | 131 | 132 | 23 |
| Q145D | 145 | 146 | 55 |
| Q145E | 145 | 146 | 46 |
| Q145K | 145 | 146 | 37 |
| Y147F | 147 | 148 | 39 |
| R158D | 158 | 159 | 64 |
| R4M | 4 | 6 | 36 |
| R4N | 4 | 6 | 52 |
| R4W | 4 | 6 | 14 |
| T95V | 95 | 96 | 15 |
| A100E | 100 | 101 | 14 |
| A100L | 100 | 101 | 23 |
| A100V | 100 | 101 | 35 |
| K102Q | 102 | 103 | 34 |
| K103I | 103 | 104 | 16 |
| K103V | 103 | 104 | 18 |
| G113F | 113 | 114 | 78 |
| G113H | 113 | 114 | 59 |
| G113K | 113 | 114 | 39 |
| G113W | 113 | 114 | 66 |
| G113Y | 113 | 114 | 68 |
| R158E | 158 | 159 | 57 |
| I212Q | 212 | 213 | 14 |
| R4Y | 4 | 6 | 52 |
| G84D | 84 | 85 | 91 |
| G84K | 84 | 85 | 81 |
| L193S | 193 | 194 | 90 |

The invention claimed is:

1. A variant having endoglucanase activity, where the variant has at least 85% sequence identity to the endoglucanase having SEQ ID NO: 1 and comprises a substitution in one or more positions corresponding to the positions of SEQ ID NO: 1 of: 4, 32, 37, 41, 44, 51, 56, 77, 80, 83, 85, 91, 93, 94, 96, 98, 103, 117, 132, 133, 134, 146, 147, 148, 152, 162, 166, 169, 179, 183, 184, 186, 201, 202, 211, or 213, and where the variant has improved stability in an aqueous composition comprising a protease in comparison with the endoglucanase having the sequence of SEQ ID NO: 1.

2. A variant having endoglucanase activity, wherein the variant has at least 85% sequence identity to amino acids 1 to 212 of SEQ ID NO: 1 or amino acids 1 to 216 of SEQ ID NO: 1.

3. The variant of claim 1, wherein the variant has a residual activity ratio (RAR) where the RAR is increased with at least 2 times the standard deviation for the assay.

4. The variant of claim 1, wherein the variant has a RAR of at least 1.1.

5. The variant of claim 1, wherein the substitutions are selected from the group consisting of: X4A, X32S, X37W, X41T, X44D, X51N, X56A, X77N, X80K, X80L, X83D, X85D, X85I, X85K, X85M, X85V, X91F, X93M, X94K, X94L, X94N, X94Q, X96A, X96F, X96R, X96V, X98T, X103A, X103L, X103M, X103Q, X117R, X132K, X132L, X132R, X132V, X133Y, X134D, X146D, X146E, X146G, X146K, X146R, X146S, X146T, X147D, X147E, X147K, X147R, X147T, X148W, X148F, X152D, X152K, X152R, X162E, X166S, X169F, X169W, X169Y, X179S, X179T, X183V, X184A, X184L, X184M, X186R, X201R, X202G, X202L, X211H, X211K, X211L, X211N, X211P, X211V, X211W, X213Q, and combinations thereof.

6. The variant of claim 5, wherein the substitutions are selected from the group consisting of: S4A, A32S, F37W, S41T, N44D, G51N, S56A, S77N, G80K, G80L, E83D, S85D, S85I, S85K, S85M, S85V, Y91F, L93M, T94K, T94L, T94N, T94Q, T96A, T96F, T96R, T96V, G98T, K103A, K103L, K103M, K103Q, G117R, I132K, I132L, I132R, I132V, F133Y, N134D, A146D, A146E, A146G, A146K, A146R, A146S, A146T, Q147D, Q147E, Q147K, Q147R, Q147T, Y148W, Y148F, S152D, S152K, S152R, A162E, P166S, Q169F, Q169W, Q169Y, D179S, D179T, F183V, T184A, T184L, T184M, Q186R, K201R, R202G, R202L, F211H, F211K, F211L, F211N, F211P, F211V, F211W, P213Q, and combinations thereof.

7. A composition comprising a variant of claim 1.

8. The composition of claim 7, further comprising a protease.

9. The composition of claim 7, further comprising one or more additional enzymes selected among: protease, lipase, cutinase, an amylase, carbohydrase, cellulase, pectinase, mannanase, arabinase, galactanase, xylanase, oxidase, e.g., a laccase, and/or peroxidase.

10. The composition of claim 7, wherein the composition is a detergent composition.

11. The composition of claim 10, further comprising one or more compounds selected among surfactants, builders and Co-builders and polymers.

12. The composition of claim 7, wherein the composition is a liquid detergent composition.

13. A method of cleaning fabric, textiles or hard surfaces, the method comprising contacting a variant of claim 1 with the fabric, textiles or hard surfaces to be cleaned.

14. A method of cleaning fabric, textiles or hard surfaces, the method comprising contacting a composition of claim 7 with the fabric, textiles or hard surfaces to be cleaned.

15. The variant of claim 1, wherein the variant has at least 85% sequence identity to the endoglucanase having SEQ ID NO: 1.

* * * * *

SEQUENCE LISTING

```
Sequence total quantity: 4
SEQ ID NO: 1           moltype = AA  length = 278
FEATURE                Location/Qualifiers
source                 1..278
                       mol_type = protein
                       organism = Thielavia terrestris
SEQUENCE: 1
ASGSGQSTRY WDCCKPSCAW PGKAAVSQPV YACDANFQRL SDFNVQSGCN GGSAYSCADQ   60
TPWAVNDNLA YGFAATSIAG GSESSWCCAC YALTFTSGPV AGKTMVVQST STGGDLGSNH  120
FDIAMPGGGV GIFNGCSSQF GGLPGAQYGG ISSRDQCDSF PAPLKPGCQW RFDWFQNADN  180
PTFTFQQVQC PAEIVARSGC KRNDDSSFPV FTPPSGGNGG TGTPTSTAPG SGQTSPGGGS  240
GCTSQKWAQC GGIGFSGCTT CVSGTTCQKL NDYYSQCL                         278

SEQ ID NO: 2           moltype = AA  length = 283
FEATURE                Location/Qualifiers
```

```
source                  1..283
                        mol_type = protein
                        organism = Humicola insolens
SEQUENCE: 2
ADGRSTRYWD CCKPSCGWAK KAPVNQPVFS CNANFQRITD FDAKSGCEPG GVAYSCADQT    60
PWAVNDDFAL GFAATSIAGS NEAGWCCACY ELTFTSGPVA GKKMVVQSTS TGGDLGSNHF   120
DLNIPGGGVG IFDGCTPQFG GLPGQRYGGI SSRNECDRFP DALKPGCYWR FDWFKNADNP   180
SFSFRQVQCP AELVARTGCR RNDDGNFPAV QISSSTSSPV NQPTSTSTTS TSTTSSPPVQ   240
PTTPSGCTAE RWAQCGGNGW SGCTTCVAGS TCTKINDWYH QCL                     283

SEQ ID NO: 3            moltype = AA  length = 295
FEATURE                 Location/Qualifiers
source                  1..295
                        mol_type = protein
                        organism = Staphylotrichum coccosporum
SEQUENCE: 3
ADGKSTRYWD CCKPSCSWPG KASVNQPVFA CSANFQRISD PNVKSGCDGG SAYACADQTP    60
WAVNDNFSYG FAATSISGGN EASWCCGCYE LTFTSGPVAG KTMVVQSTST GGDLGTNHFD   120
LAMPGGGVGI FDGCSPQFGG LAGDRYGGVS SRSQCDSFPA ALKPGCYWRF DWFKNADNPT   180
FTFRQVQCPS ELVARTGCRR NDDGNFPVFT PPSGGQSSSS SSSSSAKPTS TSTSTTSTKA   240
TSTTSTASSQ TSSSTGGGCA AQRWAQCGGI GFSGCTTCVS GTTCNKQNDW YSQCL         295

SEQ ID NO: 4            moltype = AA  length = 277
FEATURE                 Location/Qualifiers
source                  1..277
                        mol_type = protein
                        organism = Acremonium thermophilum
SEQUENCE: 4
ALDGKSTRYW DCCKPSCGWP GKASVNQPVF SCSADWQRIS DFNAKSGCDG GSAYSCADQT    60
PWAVNDNFSY GFAATAIAGG SESSWCCACY ALTFNSGPVA GKTMVVQSTS TGGDLGSNQF   120
DLAIPGGGVG IFNGCASQFG GLPGAQYGGI SDRSQCSSFP APLQPGCQWR FDWFQNADNP   180
TFTFQRVQCP SELTSRTGCK RDDDASYPVF NPPSGGSPST TSTTTSSPSG PTGNPPGGGG   240
CTAQKWAQCG GTGFTGCTTC VSGTTCQVQN QWYSQCL                             277
```